United States Patent [19]

Niedermann et al.

[11] Patent Number: 5,759,956
[45] Date of Patent: Jun. 2, 1998

[54] HERBICIDAL COMPOUNDS

[75] Inventors: Hans-Peter Niedermann, Bubenheim; Rudi Eisenacht, Mainz, both of Germany

[73] Assignee: American Cyanamid Company, Parsippany, N.J.

[21] Appl. No.: 553,298

[22] PCT Filed: May 26, 1994

[86] PCT No.: PCT/EP94/01759

§ 371 Date: May 8, 1996

§ 102(e) Date: May 8, 1996

[87] PCT Pub. No.: WO94/27974

PCT Pub. Date: Dec. 8, 1994

[30] Foreign Application Priority Data

May 27, 1993 [EP] European Pat. Off. ............. 93108536

[51] Int. Cl.$^6$ .............. C07D 241/18; C07D 401/12; C07D 403/12; A01N 43/60
[52] U.S. Cl. .............. 504/235; 544/405; 544/406; 544/407
[58] Field of Search .............. 544/319, 405, 544/406, 407, 408; 504/235, 242

[56] References Cited

U.S. PATENT DOCUMENTS

| | | | |
|---|---|---|---|
| 4,427,437 | 1/1984 | Serban et al. | 71/92 |
| 5,294,597 | 3/1994 | Foster et al. | 504/255 |
| 5,444,060 | 8/1995 | Urushibat et al. | 514/25.6 |
| 5,506,192 | 4/1996 | Anderson et al. | 504/243 |

FOREIGN PATENT DOCUMENTS

| | | |
|---|---|---|
| 488474 A1 | 6/1992 | European Pat. Off. |
| 537816 A1 | 4/1993 | European Pat. Off. |
| 2013357 | 10/1971 | Germany. |
| 4426346 | 2/1996 | Germany. |

OTHER PUBLICATIONS

Russ et al., Chemical Abstracts, vol. 118, 234003, 1993.
Chemical Abstracts, vol. 90, No. 1, Abstract No. 6352w (1979).
Chemical Abstracts, vol. 54, No. 18, col. No. 18537D (1960).
Chemical Abstracts, vol. 113, No. 17, Abstract No. 148860e (1990).
Nakamura et al., "Structure–Activity Relationship of Herbicidal 2.3–Dicvano–5–Substituted Pyrazines", Agric. Biol. Chem., 47(7), pp. 1555–1560, 1983.

*Primary Examiner*—Matthew V. Grumbling
*Assistant Examiner*—Deepak R. Rao
*Attorney, Agent, or Firm*—Gregory M. Hill

[57] ABSTRACT

A compound of the general formula (I)

wherein
A represents a group of general formula and $R^1$, $R^2$, $R^3$, $R^4$, $R^5$, $R^6$, $X$, $Q^2$, $Q^3$, and n are as described in the specification. The compounds of formula (I) are useful as agricultural herbicides.

8 Claims, No Drawings

HERBICIDAL COMPOUNDS

This is a 35 U.S.C. §371 application of PCT/EP94/01759 filed May 26, 1994.

The present invention relates to herbicidal compounds, and in particular to herbicidal carboxamide derivatives, their preparation and their use.

European Patent Specification No. 0 488 474 A1 describes and claims phenoxypicolinamides of the general formula

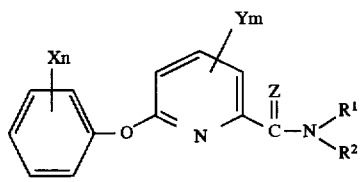

wherein n is an integer from 1 to 5 and the or each X independently represents a hydrogen or halogen atom, an alkyl or alkoxy group optionally substituted by one or more of the same or different substituents selected from halogen atoms and cyano, hydroxy and alkoxy groups, or a cyano, nitro, alkenyloxy, alkynyloxy, alkylthio, haloalkylthio, alkenylthio or alkynylthio group;

m is 0 or an integer from 1 to 3 and the or each Y independently represents a halogen atom or an alkyl or haloalkyl group;

Z represents an oxygen atom or a sulphur atom; and $R^1$ and $R^2$ each, independently, represents a hydrogen atom, an alkyl group optionally substituted by one or more of the same or different substituents selected from halogen atoms or hydroxy, cyano, alkoxy, alkylthio, alkoxycarbonyl, or mono- or di-alkylamino groups, an alkenyl, alkynyl, cycloalkyl, or optionally substituted cycloalkylalkyl group, or a hydroxy, alkoxy, alkenyloxy, alkynyloxy, alkoxycarbonyl, amino, mono- or di-alkylamino, alkoxycarbonylamino group, an arylamino group optionally substituted by a halogen atom, or a dialkylcarbamoyl group; or $R^1$ and $R^2$ together represent an alkylene chain which is optionally interrupted by an oxygen or sulphur atom or by a group —NR— in which R represents a hydrogen atom or an alkyl group.

These compounds are shown to have herbicidal properties.

Variation of the central ring of such compounds and of related pyridyloxy- and pyrazolyloxy- derivatives, to include additional hetero atoms have now been found to show high herbicidal activity. Useful intermediates to such new compounds have also been found to exhibit herbicidal properties.

The present invention accordingly provides a compound of the general formula

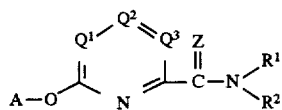

(I)

wherein

A represents a group of the general formula

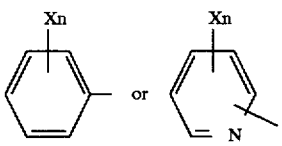

in which the or each X independently represents a halogen atom or an optionally substituted alkyl, alkoxy, aryl or aryloxy group, or an alkenyloxy, alkynyloxy, alkylthio, haloalkylthio, alkenylthio, alkenylthio, alkylsulphinyl, alkylsulphonyl or cyano group; and n is 0, an integer from 1 to 4, or, for the phenyl group, 5; or A represents a group of the general formula

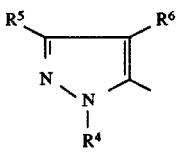

in which each of $R^4$, $R^5$ and $R^6$ independently represents a hydrogen or halogen atom, an optionally substituted alkyl, alkenyl, alkynyl, cycloalkyl, cycloalkylalkyl, aryl, aralkyl, alkaryl, alkoxy, amino, mono- or di-alkylamino, alkoxycarbonylamino, arylamino, dialkylcarbamoyl, acyl or acylamido group or a cyano group, with the proviso that $R^5$ and $R^6$ do not represent an acyl, acylamido or cyano group;

Z represents an oxygen or sulphur atom;

$R^1$ and $R^2$ each independently represents a hydrogen atom or an optionally substituted alkyl, alkenyl, alkynyl, cycloalkyl, cycloalkylalkyl, heterocyclyl, aryl, aralkyl, alkaryl, hydroxy, alkoxy, alkenyloxy, alkynyloxy, alkylcarbonyl, alkoxycarbonyl, amino, mono- or di-alkylamino, alkoxycarbonylamino, arylamino, arylalkylamino or dialkylcarbamoyl group, or together represent an alkylene chain which is optionally interrupted by an oxygen or sulphur atom or by a group —$N^7$— in which $R^7$ represents a hydrogen atom or an alkyl group; and $Q^1$, $Q^2$ and $Q^3$ each represents a nitrogen atom or a group $CR^3$ in which $R^3$ represents a hydrogen atom or an optionally substituted alkyl, alkoxy, alkylthio or mono- or di-alkylamino group, provided that all three of $Q^1$, $Q^2$ and $Q^3$ are not a nitrogen atom or the group $CR^3$.

Generally, herein, any alkyl, alkenyl or alkynyl moiety which is or forms part of a group represented by X, $R^1$, $R^2$, $R^3$, $R^4$, $R^5$, $R^6$ or $R^7$ suitably contains up to 12 carbon atoms, conveniently up to 8, preferably up to 6, and especially up to 4, carbon atoms. Such moieties may be linear or branched chain moieties. As part of a larger group, alkyl moieties are especially methyl or ethyl.

A cycloalkyl moiety suitably contains from 3 to 10, preferably from 3 to 8, carbon atoms. An aryl group is usefully a single ring or fused ring system having from 6 to 14 ring members, preferably 6 or 10 ring atoms; a preferred aryl group is phenyl.

A heterocyclic group is suitably a single ring system having 3 to 6 ring members selected from carbon atoms and at least one nitrogen, oxygen or sulphur atom; preferred heterocyclic groups are morpholino and thienyl.

Halogen is used to denote fluorine, chlorine, bromine or iodine, especially chlorine or fluorine. A preferred haloalkyl moiety is trifluoromethyl.

An acyl group is the group formed by the removal of hydroxyl from a carboxyl group, and is used herein to include formyl and optionally substituted alkylcarbonyl and arylcarbonyl groups.

An alkylene chain suitably has from 3 to 6, preferably 4 or 5 chain members.

Optional substituents may be any of those customarily employed in the development of biocidal compounds, and/or the modification of such compounds to influence their activity, persistence, penetration or any other property. Specific examples of such substituents include halogen, especially fluorine, chlorine or bromine atoms, and phenyl, nitro, cyano, amino, hydroxy, alkyl, alkoxy, mono- or di-alkylamino groups, haloalkyl, haloalkoxy, formyl, alkoxycarbonyl, carboxy, halophenyl groups and heterocyclyl, especially thienyl, groups. Alkyl moieties of such optional substituents usefully have from 1 to 6 carbon atoms, preferably 1 or 2 carbon atoms.

Where group A represents a phenyl or pyridyl ring, the substituent(s) X, if present, may be at any of the free positions on the ring. Preferably a substituent X is present meta to the bond to the oxygen atom of formula I. Especially useful examples of the substituent(s) X include halogen atoms and haloalkyl groups. Preferably X represents a chlorine atom or a trifluorimethyl group. There are usefully either no X substituents or, preferably, only 1 X substituent.

Where A represents a pyrazolyl group, preferably $R^6$ represents a hydrogen atom, and each of $R^4$ and $R^5$ independently represents an alkyl, cycloalkyl, haloalkyl or an aryl group, more preferably a $C_{1-4}$ alkyl, or halo($C_{1-2}$) alkyl group, especially a methyl or trifluoroalkyl group. Preferably, $R^4$ represents a methyl group and $R^5$ represents a methyl or trifluoromethyl group.

It is especially preferred that A represents a 3-trifluoromethylphenyl group.

Z preferably represents an oxygen atom.

The substituents $R^1$ and $R^2$ may be the same or different. Preferably each of $R^1$ and $R^2$ represents a hydrogen atom, a $C_{1-6}$ alkyl group, a $C_{3-6}$ cycloalkyl group or a phenyl group which is unsubstituted or halo-substituted. Examples of such preferred meanings include one of $R^1$ and $R^2$ representing a hydrogen atom or a $C_{1-4}$ alkyl group, eg ethyl, whilst the other represent a hydrogen atom, a $C_{1-6}$ alkyl group, eg ethyl, whilst the other represents a hydrogen atom, a $C_{1-6}$ alkyl group, eg butyl, a cyclopropyl group, a phenyl group or a fluorophenyl group, eg 4-fluorophenyl or 2,4-difluorophenyl.

Especially preferred are compounds in which one of $R^1$ and $R^2$ is hydrogen or ethyl and the other is 4-fluorophenyl.

The central ring of the compounds of formula I is a heteroaryl ring in which at least 2 of the ring members are nitrogen atoms. Examples of such rings include pyrimidine, pyrazine and triazine rings.

Preferably, one of $Q^1$, $Q^2$ and $Q^3$ represents a nitrogen atom, a second represents the group $CR^3$ in which $R^3$ represents a hydrogen atom, a $C_{1-4}$ alkyl group or a di($C_{1-4}$)alkylamino, eg dimethylamino, group, and the third represents the group =CH—. Thus preferably the central ring is an optionally substituted pyrimidine or pyrazine ring. Especially preferred are compounds in which the central ring is an unsubstituted pyrimidine or pyrazine ring or a 6-methyl- pyrimidinyl group.

The present invention further provides a process for the preparation of a compound of general formula I, which comprises reacting a compound of the general formula II

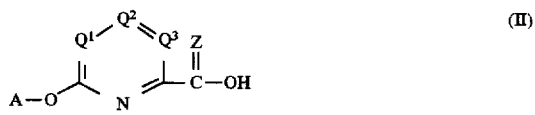

in which A, Z, $Q^1$, $Q^2$ and $Q^3$ are as defined above, or an activated derivative thereof, with a compound of the general formula III

in which $R^1$ and $R^2$ are as defined above, or, for a compound of the invention in which $Q^1$ and $Q^3$ are both nitrogen and $Q^2$ is the group =CH—, cyclising a compound of the general formula IV

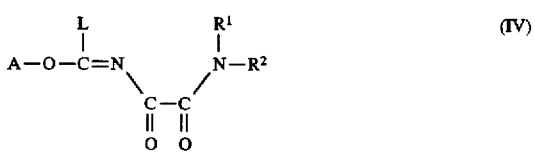

in which A, $R^1$ and $R^2$ are as defined above, and L represents a leaving group, by reaction with an isothiourea, and converting the resulting thio-substituted compound into a compound of the invention by removal or replacement of the thio substituent.

A leaving group is any group that will, under the reaction conditions, cleave from the starting material, thus enabling substitution at that specific site. The leaving group L may suitably be a halogen atom, for example a bromine atom or, especially a chlorine atom, an alkoxy group, suitably $C_{1-4}$ alkoxy, especially methoxy, an alkyl- or aryl-sulphonium group, especially a $C_{1-6}$ alkyl-, phenyl- or tolyl-sulphonium group, or an alkyl- or aryl-sulphonic acid group, especially a $C_{1-6}$ alkyl-, phenyl- or tolyl-sulphonic acid group.

Activated derivatives of the compounds or the general formula II are compounds in which the hydroxy group of the acid function has been replaced by a suitable leaving group, for instance a halogen atom, for example a bromine atom, or especially, a chlorine atom, an alkoxy group, suitably $C_{1-4}$ alkoxy, especially methoxy, or an imidazole group. Preparation of an activated derivative may be effected by conventional means, for example the acid chloride may be prepared using thionyl chloride.

The process of the invention is suitably carried out in the presence of an inert organic solvent, for example dimethylformamide or dimethylsulphoxide, or an aromatic hydrocarbon, for example benzene or toluene, or a halogenated hydrocarbon, for example dichloromethane, or an ether, for example diethyl ether, or an ester, for example ethyl acetate. The process is suitably carried out at a temperature in the range of from 0° to 100° C., preferably at the reflux temperature of the reaction mixture, and suitably in the presence of a base, for example potassium hydroxide, and a copper catalyst, such as cuprous chloride.

Suitably the reaction is carried out using substantially equimolar amounts of the reactants. However, it can be expedient to use one reactant in excess.

When the compounds of formula I are prepared from an acid halide derivative of the compound of formula II, the reaction is conveniently carried out at a temperature in the range of from 0° to 50° C., preferably at ambient temperature, and suitably in the presence of a base, for example potassium carbonate or, preferably, an amine base, such as triethylamine.

Other activated derivatives may require different reaction conditions which will be within the knowledge of the skilled person in the art, or easily ascertainable by such by routine experimentation. For an ester derivative (where the hydroxy function has been replaced by an alkoxy group), the reaction is suitably carried out at a temperature in the range of from 0° to 100° C., preferably at ambient temperature, and in the absence of an added base.

Compounds of formula I in which Z represents a sulphur atom may be prepared from a compound of formula I in which Z represents an oxygen atom by reaction with phosphorous pentasulphide under standard conditions, for example by heating, suitably under reflux, in the presence of an inert aromatic solvent, for example benzene, toluene, pyridine or quinoline.

The compounds of the present invention may be isolated and purified by conventional techniques, for example by solvent extraction, evaporation followed by recrystallisation, or by chromatography on silica or alumina.

The compounds of formula II may be prepared by hydrolysis of cyano derivatives of the general formula V

(V)

in which A, $Q^1$, $Q^2$ and $Q^3$ have the meanings given above.

This reaction is suitably carried out in the presence of a solvent which is inert with respect to the reaction components, for example water, or ethylene glycol, using as hydrolysis reactants acids such as hydrochloric acid, sulphuric acid, or, for the pyridyloxy compounds of formula V, phosphoric acid, or bases such as potassium hydroxide or sodium hydroxide, at a temperature in the range of from 0° to 150° C., for example at reflux. It is not essential for an inert solvent to be used; the reaction may still proceed if the cyano compound V is suspended in the hydrolysis reactant.

It is possible via this reaction to prepare compounds of formula I in which each of $R^1$ and $R^2$ represents a hydrogen atom, in addition to the acid intermediate. Isolation of the carbamide is possible via solvent extraction and chromatography on silica gel. Compounds of formula V may suitably be prepared by reacting a compound of the general formula VI

(VI)

in which $Q^1$, $Q^2$ and $Q^3$ are as hereinbefore defined, and Y is a leaving group as defined above, preferably a halogen atom, especially chlorine, with a compound of formula VII

A—OH or an alkali metal salt thereof. Suitable reaction conditions are the same as those specified above for the reaction of compounds of formulae II and III.

Compounds of formula VI may be prepared by conventional or literature methods, such as the procedure of Daves et al., J. Het. Chem. 1 (1964), 130.

It is also possible to prepare the cyano compounds of formula V by conversion of an appropriate precursor group of corresponding compounds, e.g. compounds corresponding to those of the formula V but with, for example, a methylsulphonyl group or a dimethylamino group in place of the cyano group. The conversion of such precursor groups is usually effected by reaction with a suitable cyanide compound, such as sodium or potassium cyanide or tertiaryalkylammonium cyanide, e.g. tertiary ethyl- or tertiary butyl-ammonium cyanide. The precursor compounds may themselves be prepared analogously to compounds of formula V by reaction of a suitably substituted heterocyclic compound (corresponding to a compound of formula VI) with a compound of formula VII or alkali metal salt thereof. Alternatively the precursor compounds may be derived from a compound of formula

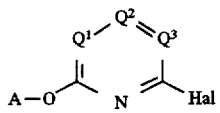

where A, $Q^1$, $Q^2$ and $Q^3$ are as previously defined and Hal is a suitable halogen leaving group, e.g. chlorine; such compounds themselves may be prepared from the constituent ring compounds analogously to the reaction of compounds VI and VII above.

The compounds of formula II may also be prepared by reacting a compound of the general formula VIII

(VIII)

in which Z, $Q^1$, $Q^2$ and $Q^3$ are as specified above, L represents a leaving group, preferably a halogen atom, for example chlorine, and AlK represents an alkyl group, for example an ethyl group, with a compound of the general formula VII, or an alkali metal salt thereof, especially a sodium salt thereof, utilising the same reaction conditions as for the reaction of compounds of formulae II and III.

The compounds of formulae II, and alkyl esters thereof, and V form further aspects of the present invention.

The compounds of formula VIII may be prepared by reaction of a compound of formula VII, or alkali metal salt thereof, with an appropriate heterocyclic compound by the general reaction conditions specified above for such reactions, utilising the necessary procedures for incorporation into the heterocyclic compound of a suitable leaving group as are available to the person skilled in the art.

The compounds of formula VII are either known or preparable by conventional or literature methods, for example by the methods of J. Het. Chem. 28 (1991), 1971 ff, and j. Het. Chem. 27 (1990), 243 ff.

For certain heterocyclic variants of the formula I, it may be necessary to use cyclisation synthesis procedures. Thus for 1,3,5-triazine compounds of formula I, i.e. in which $Q^1$ and $Q^3$ are both nitrogen and $Q^2$ is a group =CH—, it is appropriate to use a preparation process which comprises cyclising a compound of the general formula IV

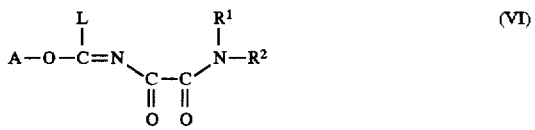
(VI)

in which A, $R^1$ and $R^2$ are as hereinbefore defined, and L represents a leaving group, preferably a halogen atom, for example chlorine, by reaction with an isothiourea, for example isothiourea itself or an S-alkyl, preferably S-methyl, isothiourea, and converting the resulting thiosubstituted compound into a compound of formula I by removal or replacement of the thio substituent.

The reaction is conveniently carried out at room temperature using a suitable tertiaryalkyl amine base, eg triethylamine, and inert solvent, eg dioxane.

Compounds of formula IV maybe prepared by the condensation of compounds of the general formula A-OCN, in which A is as hereinbefore defined, with an appropriate oxalic half anilide half halide at elevated temperature, for example a temperature in the range of from 30° C. to 60° C., and in the presence of an inert solvent, eg dioxane. The cyanate compounds may be prepared by conventional procedures from a compounds of formula VII by reaction with a cyanogen halide, for example cyanogen bromide.

Compounds of formula I and alkyl esters of compounds of formula II and compounds of formula V have been found to have useful herbicidal activity. Accordingly, the present invention further provides a herbicidal composition which comprises a compound of formula I or a compound of formula II or an alkyl ester thereof or a compound of formula V in association with a carrier, and a method of making such a composition which comprises bringing a compound of formula I into association with a carrier.

The invention further provides the use of a compound of formula I or of a compound of formula II or an alkyl ester thereof or a compound of formula V or of a composition of the invention, as a herbicide. Also provided is a method of combating undesired plant growth at a locus by treating the locus with a compound of formula I, with a compound of formula II or an alkyl ester thereof or compound of formula V or a composition of the invention. The locus may be, for example, the soil or plants in a crop area. The dosage of active ingredient used may, for example, be in the range of from 0.01 to 10 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone;

ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic.

Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate;

and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–0% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

EXAMPLES 1 to 8

EXAMPLE 1

Preparation of 2-(3-trifluoromethylphenoxy) pyrimidine-4-carbamide and of 2-(3-trifluoromethylphenoxy)-pyrimidine-4-(N-(4-fluorophenyl)) carboxamide Compound 1—2-(3-Trifluoromethylphenoxy)pyrimidine-4-carbonitrile The starting material, 2-chloropyrimidine-4-carbonitrile, was prepared according to the procedure of Daves et al. (J. Het. Chem. 1, (1964), 130).

1.6 g 3-trifluoromethylphenol was dissolved in 50 ml of toluene and 1.8 g of Na-methylate solution (30% in methanol) was added and stirred. After 10 minutes the solution was evaporated to dryness. A solution of 1.4 g 2-chloropyrimidine-4-carbonitrile in 15 ml dimethylformamide was added and the mixture stirred for 10 minutes and evaporated to dryness. The residue was dissolved in 50 ml ethyl acetate and washed with 50 ml water. The organic layer was dried with $Na_2SO_4$ and evaporated. The residue was purified on silica gel with toluene/ethyl acetate as eluant to give 2.3 g (86.8%) of pure 2-(3-trifluoromethylphenoxy) pyrimidine-4- carbonitrile.

NMR $(CDCl_3)$:7.3–7.5(m,4H,Arom.);7.55(d,1H,Arom.); 8.7(d,1H,Arom.)

Compound 2—2-(3-trifluoromethylphenoxy)pyrimidine-4-carbamide and
Compound 3—2-(3-trifluoromethylphenoxy)pyrimidine-4-carboxylic acid 7.8 g of 2-(3-trifluoromethylphenoxy)pyrimidine-4-carbonitrile (prepared as above) and 17 ml conc. HCl were stirred for 45 minutes at 65° C., cooled to room temperature and diluted with 80 ml water. The residue was collected, dissolved in 50 ml ethyl acetate and extracted twice with 50 ml 0.1N NaOH. The water layer was acidified with conc. HCl and the 2-(3-trifluoromethylphenoxy)-pyrimidine-4-carboxylic acid collected and dried to give 1.4 g (17.4%) of white crystals with m.p. 180°–183° C. (with decomposition). The organic layer was evaporated and the residue was purified on silica gel with toluene/ethylacetate as eluent to give 3.7 g (44.4%) 2-(3-trifluoromethylphenoxy)-pyrimidine-4-carbamide as white crystals of m.p. 113° C.

Compound 4—2-(3-trifluoromethylphenoxy)pyrimidine-4-(N-(4-fluorophenyl))-carboxamide 1.0 g of 2-(3-trifluoromethylphenoxy)pyrimidine-4-carboxylic acid (prepared as above) was dissolved in 5 ml $SOCl_2$, drop of dimethylformamide was added and the mixture stirred at reflux temperature for 30 minutes, excess $SOCl_2$ distilled off, 10 ml of toluene added and evaporated. The residue was dissolved in 15 ml of toluene and added over 3 minutes to a solution of 0.4 g 4-fluoroaniline and 0.4 g of triethylamine in 20 ml toluene and stirred for 5 minutes at room temperature. The mixture was poured into 30 ml of water, the organic layer was washed with 20 ml dil. HCl, 20 ml water, 20 ml dil. $Na_2CO_3$-solution and finally with 20 ml of water, dried over $Na_2SO_4$ and evaporated to give 1.27 g (96%) of white crystals of Compound 4, of m.p. (83°–92° C.).

EXAMPLES 2

Table 1 contains compounds nos. 5 to 9 synthesised according to the procedure of Example 1.

TABLE 1

| Compound No. | $R_1$ | $R_2$ | m.p. (°C.) | yield (%) |
|---|---|---|---|---|
| 5 | H | $C_6H_5$ | 60–61 | 37.9 |
| 6 | $C_2H_5$ | $C_6H_5$ | 81–87 | 51.3 |
| 7 | H | $CH_2CH(CH_3)_2$ | oil | 34.2 |
| 8 | H | 2,4-di-F—$C_6H_3$ | 79 | 41.5 |
| 9 | H | cyclopropyl | oil | 38.7 |

EXAMPLE 3

Preparation of 4-(3-trifluoromethylphenoxy) pyrimidine-2-carbamide and 4-(3-trifluoromethylphenoxy)pyrimidine-2-(N-(4-fluorophenyl)) carboxamide Compound 10—2-Chloro-4-(3-trifluoromethylphenoxy)pyrimidine 16.21 g of 3-trifluoromethylphenol was dissolved in 18 g 30% sodium methylate solution, stirred for 10 minutes and evaporated to dryness, the residue dissolved in toluene and again evaporated to dryness. A solution of 14.9 g 2,4-dichloropyrimidine in 50 ml dimethylformamide was added at room temperature and the mixture stirred for 15 minutes. The solution was reduced to 5 ml, poured into 50 ml water and extracted twice with 50 ml ethyl acetate. The combined organic layers were dried over $Na_2SO_4$, evaporated and the residue was purified on silica gel with toluene/ethyl acetate to give 18.3 g (66.6%) of white crystals of Compound 10 of m.p. 48°–53° C.

Compound 11—2-Cyano-4-(3-trifluoromethylphenoxy) pyrimidine To a solution of 0.66 g trimethylamine in 20 g dimethylformamide were added 2.8 g of 2-chloro-4-(3-trifluoromethylphenoxy)pyrimidine (prepared as above) at 0° C. at 0° C. The solution was allowed to warm to room temperature with stirring for 3.5 hours. 1.6 g tetraethylammonium cyanide were added in one portion and the mixture stirred for another 30 minutes. The solution was then diluted with 100 ml of water and extracted three times with 50 ml ethyl acetate. The combined organic layers were dried over $Na_2SO_4$, evaporated and the residue was purified on silica gel with toluene/ethyl acetate to give 2.2 g (83%) of pale yellow crystals of Compound 11, m.p. 56° C.

Compound 12—4-(3-trifluoromethylphenoxy)pyrimidine-2-carbamide
Compound 13—4-(3-trifluoromethylphenoxy)pyrimidine-2-carboxylic acid 5.3 g of 2-cyano-4-(3-trifluoromethylphenoxy)pyrimidine (prepared as above) were suspended in 10 ml conc. HCl and stirred at 80° C. for 1 hour. After cooling to room temperature, the solution was made basic with NaOH and extracted twice with 50 ml ethyl acetate. The combined organic layers were dried over $Na_2SO_4$, evaporated and the residue was purified on silica gel with toluene/ethyl acetate as eluent to give 1.8 g (31.8%) of 4-(3-trifluoromethylphenoxy)pyrimindine-4-carbamide of m.p. 107° C. The alkaline water layer was acidified with conc.

HCl and extracted three times with 50 ml ethyl acetate. The combined ethyl acetate layers were dried over $Na_2SO_4$ and evaporated to dryness to give 0.44 g (7.8%) of 4-(3-trifluoromethylphenoxy)pyrimidine-2-carboxylic acid, m.pt. 143° C. (with decomposition).

Compound 14—4-(3-trifluoromethylphenoxy)pyrimidine-2-N-(4-fluorophenyl)carboxamide Analogously to the preparation of Compound 4 [2-(3-trifluoromethylphenoxy)pyrimidine-4-(N-(4-fluorophenyl))carboxamide]0.44 g of 4-(3-trifluoromethylphenoxy)pyrimidine-2-carboxylic acid gave, after purification on silica gel with toluene/ethyl acetate as eluent, 0.41 g (70.7%) of pure 4-(3-trifluoromethylphenoxy)-pyrimidine-2-(N-(4-fluorophenyl)) carboxamide as white crystals of m.p. 113° C.

EXAMPLE 4

Preparation of 4-(trifluoromethyl)phenoxy-6-(N,N-dimethylamino)pyrimidine-2-(N-(4-fluorophenyl)) carboxamide Compound 15—2-methylthio-4-chloro-6-(N,N-dimethylamino) pyrimidine To a solution of 46 g 2-methylthio-4,6-dichloropyrimidine in 250 ml dioxane, were added at room temperature and over a period of 10 minutes, 65.6 ml of 40% dimethylammonia-solution in water and the mixture was stirred for one hour. The solvent was evaporated and the residue purified on silica gel with toluene as eluent to give 57.0 g (97.9%) of 2-methylthio-4-chloro-6-(N,N-dimethylamino)-pyrimidine of m.p. 102° C.

Compound 16—2-methylthio-4-(3-trifluoromethyl)phenoxy-6-(N,N-dimethylamino) pyrimidine A solution of 8.1 g of 3-trifluoromethylphenol and 9.0 g $NaOCH_3$-solution (30%) in 200 ml toluene was stirred for 20 minutes and the mixture was evaporated to dryness. The residue was dissolved in 20 ml dimethylsulphoxide and 10.18 g of 2-methylthio-4-chloro-6-(N,N-dimethylamino) pyrimidine (prepared as above) were added and the solution was stirred for 18 hours at 135° C. After cooling to room temperature the solution was poured into 200 ml of water and extracted twice with 50 ml of ethyl acetate. The combined ethyl acetate layers were dried over $Na_2So_4$ and evaporated to dryness. The residue was purified on silica gel with toluene as eluent to give 14.48 g (88%) of pure 2-methylthio-4-(3-trifluoro-methyl)phenoxy-6-(N,N-dimethylamino)-pyrimidine of m.p. 108° C.

Compound 16(A). Following similar procedure, 2-methylthio-4-(2-chloropyrid-4-yloxy)-6-(N,N-dimethylamino)-pyrimidine was prepared in 45.2% yield; m.pt. 98°–99° C.

Compound 17—2-Methylsulfonyl-4-(3-trifluoromethyl)phenoxy-6-(N,N-dimethylamino) pyrimidine 3.3 g of 2-methylthio-4-(3-trifluoromethyl)phenoxy-6-(N,N-di-methylamino)pyrimidine (prepared as above) were dissolved in 50 ml trichloromethane and 5 g of m-chloroperbenzoic acid were added over a period of 5 minutes at 0° C. The mixture was stirred for 15 minutes and allowed to come to room temperature. The precipitated m-chlorobenzoic acid was filtered off and washed with 20 ml of trichloromethane. The filtrate was reduced and the residue was purified on silica gel with toluene/ethyl acetate as eluent to give 13.5 g (94.9%) of pure 2-methylsulfonyl-4-(3-trifluoromethyl)-phenoxy-6-(N,N-dimethylamino) pyrimidine of m.p. 91°–92° C.

Compound 17(A). Following a similar procedure, 2-methylsulphonyl-4-(2-chloropyrid-4-yloxy)-6-(N,N-dimethyl-amino)-pyrimidine was prepared in 54.7% yield; m.pt. 89° C.

Compound 18—2-Cyano-4-(3-trifluoromethyl)phenoxy-6-(N,N-dimethyl-amino)pyrimidine 1.7g of 2-methylsulfonyl-4-(3-trifluoromethyl)phenoxy-6-(N,N-dimethylamino)pyrimidine (prepared as above) and 0.3 g of KCN were dissolved in 8 ml dimethylformamide and the mixture was stirred at 110° C. for 45 minutes. After cooling to room temperature the mixture was poured into 100 ml of water and was extracted twice with 50 ml ethyl acetate. The combined organic layers were dried over $Na_2SO_4$ and evaporated. The residue was purified on silica gel with toluene as eluent to give 1.1 g (75.9%) of 2-cyano-4-(3-tri- fluoromethyl)phenoxy-6-(N,N-dimethylamino) pyrimidine of m.p. 88°–92° C.

Compound 18(A). Following a similar procedure, 2-cyano-4-(2-chlorpyrid-4-yloxy)-6-(N,N-dimethylamino) pyrimidine was prepared in 40.8% yield; pt. 98°–108° C.

Compound 19—4-(trifluoromethyl)phenoxy-6-(N,N-dimethylamino)-pyrimidine-2-carboxylic acid 2.5 g NaOH were dissolved in 50 ml water and 4.5 g of 2-cyano-4-(3-trifluoromethyl)phenoxy-6-(N,N-dimethylamino) pyrimidine (prepared as above) were added and the mixture was refluxed for 5 hours. After cooling the mixture was extracted twice with 20 ml ethyl acetate and the alkaline aqueous solution was acidified with glacial acetic acid. The acid water solution was extracted four times with 50 ml ethyl acetate and the combined organic layers were dried over $Na_2SO_4$ and evaporated to give 3.8 g (77.4%) of pale yellow crystals of 4-(trifluoromethyl)phenoxy-6-(N,N-dimethylamino)pyrimidine-2-carboxylic acid of m.p. 110°–114° C.

Compound 20—4-(Trifluoromethyl)phenoxy-6-(N,N-dimethylamino)-pyrimidine-2-(N-(4-fluorophenyl)) carboxamide 0.98g of 4-(trifluoromethyl)phenoxy-6-(N,N-dimethylamino)- pyrimidine-2-carboxylic acid (prepared as above) were dissolved in 2 ml of $SOCl_2$ and refluxed for 10 minutes. The solution was evaporated and 10 ml of toluene were added and the mixture stirred for 5 minutes and evaporated again. The residue was dissolved in 20 ml of toluene and a solution of 0.6 g triethylamine and 0.34 g of 4-fluoroaniline in 20 ml of toluene was added and the mixture was stirred for 15 minutes at room temperature. After pouring into 100 ml water the organic layer was separated and the water phase was extracted twice with 75 ml of toluene. The combined organic layers were extracted twice with 20 ml of dil. HCl and once with 50 ml of water, dried over $Na_2SO_4$ and evaporated to dryness. The residue was purified on silica gel with toluene/ethyl acetate to give 0.81 g (64.3%) of 4-(trifluoromethyl)phenoxy-6-(N,N-dimethyl-amino)pyrimidine-2-(N-(4-fluorophenyl)) carboxamide of m.p. 148°–149° C.

Compound 20(A). Following a similar procedure, 4-(2-chloropyrid-4-yloxy)-6-(N,N-dimethylamino)pyrimidine-2-(N-(4-fluorophenyl))carboxamide was prepared in 91.1% yield; m.pt. 157°–163° C.

EXAMPLE 5

Table 2 contains compounds synthesised according to the procedure of Example 4.

TABLE 2

[Structure: compound with H₃C—N—CH₃ group, R₁R₂N—C(=O)— group, and phenoxy-CF₃ substituent]

| Compound No. | R₁ | R₂ | m.p. (°C.) | yield (%) |
|---|---|---|---|---|
| 21 | H | 2,4-di-F—C₆H₃ | 141 | 64.7 |
| 22 | H | C₆H₅ | 93 | 75.5 |
| 23 | C₂H₅ | C₆H₅ | oil | 79.9 |
| 24 | H | H | 216 | 15.3 |

Compound 23 NMR (CDCl$_3$): 1.3(t, 3H, CH$_3$); 3.0(s, 6H, N(CH$_3$)$_2$); 3.8(q, 2H, CH$_2$); 5.6(s, 1H); 6.9–7.4(m, 9H, Arom.).

EXAMPLE 6

Preparation of 6-(3-trifluoromethyl) phenoxypyrazine-2-(N-(4-fluorophenyl)carboxamide Compound 25—Ethyl pyrazine carboxylate To 20 g of pyrazine carboxylic acid were added 25 ml of SOCl$_2$ and the mixture was refluxed for 30 minutes, evaporated, the residue was dissolved in 30 m. of toluene and evaporated again.

The residue was dissolved in 50 ml toluene and dropped into 150 ml ethanol over a period of 30 minutes and the resulting mixture was stirred overnight at room temperature. Evaporation and filtration on silica gel with ethyl acetate yielded 23.3 g (93.9%) of an orange oil which solidified overnight to crystals of m.p. 45° C.

Compound 26—Ethyl pyrazine carboxylate-4-oxide 3.4 g hydrogen peroxide (30%) was added in three portions over a period of 1 hour to a solution of 3.06 g of ethyl pyrazine carboxylate (prepared as above) in 15 ml of glacial acetic acid at 65° C. After stirring for 16 hours another 3.4 g hydrogen peroxide were added and the solution was stirred for 48 additional hours. The volume of the mixture was reduced, 30 ml of ethanol were added and the solution was filtered. The liquid was evaporated and the residue purified on silica gel with toluene/ethyl acetate to give 0.5 g (14.80) of white ethyl pyrazinecarboxylate-4-oxide; m.pt. 128° C.

Compound 27—Ethyl 6-chloropyrazine-2-carboxylate 2.3 g of ethyl pyrazine carboxylate-4-oxide (prepared as above), 12 ml POCl$_3$ and 20 ml of toluene were mixed and stirred for 1 hour at 90°–100° C. After cooling 50 ml of ice water were added, the solution was made basic with sufficient Na$_2$SO$_3$ solution and extracted twice with 30 ml ethyl acetate. The combined organic layers were dried over Na$_2$SO$_4$ and evaporated to give 2.5 g (100%) of a dark brown oil which was used for further reaction without purification.

NMR(CDCl$_3$):1.45(t,3H,CH$_3$); 4.5(q,2H,CH$_2$); 8.8(s,1H, Arom.); 9.2 (s,1H,Arom.)

Compound 28—Ethyl 6-(3-trifluoromethyl)-henoxyoyrazine-2-carboxylate

To a solution of 2.87 g sodium phenolate in 30 ml dimethyl-formamide were added 2.9 g ethyl 6-chloropyrazine-2-carboxylate (prepared as above) and the mixture was stirred for 1 hour at 80° C. After evaporation the residue was diluted with water and extracted twice with 50 ml ethyl acetate. The combined organic layers were dried over Na$_2$SO$_4$ evaporated, and the residue was separated on silica gel with petroleum/methyl tert.butyl ether to give 3.95 g (81.4%) of white crystals, m.p. 80.50° C.—Compound 27.

Analogous to the above procedure, the compounds in Table 3 have been prepared

TABLE 3

[Structure: R—O-pyrazine-C(=O)—OR₁]

| Compound No. | R | R₁ | mp °C. | % yield |
|---|---|---|---|---|
| 29 | 1-CH$_3$-3-CF$_3$-pyrazol-5-yl | —C$_3$H$_9$ | 74 | 63.3 |
| 30 | 3-CF$_3$-4-F—C$_6$—H$_4$ | —C$_2$H$_5$ | 69–1 | 18.9 |

Compound 31—6-(3-Trifluoromethyl)phenoxypyrazine-2-carboxylic acid 4.92 g of ethyl 6-(3-trifluoromethyl)phenoxy-yrazine-2-carboxylate were dissolved in 40 ml ethanol, 8.5 ml of 2N NaOH were added and the mixture was refluxed for 1 hour. After cooling the solvent was distilled off, the residue was dissolved in 5 ml water and the solution was acidified with 2N HCl. The precipitate was separated by filtration to give 3.7 g (92.5%) of white crystals of m.p. 118° C.

Following the above procedure, analogous compounds listed in Table 4 have been prepared.

TABLE 4

[Structure: R—O-pyrazine-C(=O)—OR₁]

| Compound No. | R | R₁ | mp °C. | % yield |
|---|---|---|---|---|
| 32 | 1-CH$_3$-3-CF$_3$-pyrazol-5-yl | H | 126–136 | 79.0 |
| 33 | 3-CF$_3$-4-F—C$_6$—H$_4$ | H | 117 | 70.9 |

Compound 34—6-(3-trifluoromethyl)-phenoxypyrazine-2-(N-(4-fluorophenyl))carboxamide To 1.07 g of 6-(3-trifluoromethyl)phenoxy-yrazine-2-carboxylic acid chloride (prepared from 1 g acid and 5 ml SOCl$_2$) were added a solution of 0.5 g 4-fluoroaniline and 0.36 g of triethylamine in 10 ml toluene at room temperature and the mixture was stirred for 15 minutes. 50 ml of ethyl acetate and 50 ml of water were added, the organic layer was separated and washed first with 50 ml dil. HCl and then with 50 ml 0.5N NaOH. After drying over Na$_2$SO$_4$ and evaporation to dryness, 1.23 g (92.6%) of slightly yellow crystals of Compound 29 were collected; m.p. 91° C.

EXAMPLE 6(A)

Table 5 contains details of further compounds synthesised according to the procedure of Example 6.

TABLE 5

| Compound No. | $R_1$ | $R_2$ | m. pt. (°C.) | yield (%) |
|---|---|---|---|---|
| 35 | H | 2,4-di-F—$C_6H_3$ | 111 | 95.9 |
| 36 | $C_2H_5$ | $C_6H_5$ | 55 | 93.0 |
| 37 | H | 2-F—$C_6H_4$ | 136 | 90.4 |

TABLE 5-continued

| Compound No. | $R_1$ | $R_2$ | m. pt. (°C.) | yield (%) |
|---|---|---|---|---|
| 38 | —$CH_2CH_2OCH_2CH_2$— | | 107–110 | 38.0 |

In analogy to the procedure for compound 34, the following compounds listed in Table 6 have been prepared.

TABLE 6

| Compound No. | R | $R_1$ | $R_2$ |
|---|---|---|---|
| 39 | 3-$CF_3$—$C_6H_4$ | H | —$C_6H_5$ |
| 40 | 3-$CF_3$—$C_6H_4$ | —$C_6H_5$ | —$C_6H_5$ |
| 41 | 3-$CF_3$—$C_6H_4$ | H | -3-F—$C_6H_4$ |
| 42 | 3-$CF_3$—$C_6H_4$ | —$CH_2CHCH_2$ | —$C_6H_5$ |
| 43 | 3-$CF_3$—$C_6H_4$ | H | -4-O$C_6H_5$—$C_6H_4$ |
| 44 | 3-$CF_3$—$C_6H_4$ | H | -cyclo-$C_3H_5$ |
| 45 | 3-$CF_3$—$C_6H_4$ | H | -i-$C_3H_7$ |
| 46 | 3-$CF_3$—$C_6H_4$ | H | —$CH_2CHCH_2$ |
| 47 | 3-$CF_3$—$C_6H_4$ | H | -n-$C_4H_9$ |
| 48 | 3-$CF_3$—$C_6H_4$ | H | —$C(CH_3)_3$ |
| 49 | 3-$CF_3$—$C_6H_4$ | H | -cyclo-$C_4H_7$ |
| 50 | 3-$CF_3$—$C_6H_4$ | H | -2-Cl-pyrid-4-yl |
| 51 | 3-$CF_3$—$C_6H_4$ | H | -n-$C_3H_7$ |
| 52 | 3-$CF_3$—$C_6H_4$ | H | —$CH_2$—$CF_3$ |
| 53 | 3-$CF_3$—$C_6H_4$ | H | -3,5-F—$C_6H_3$ |
| 54 | 3-$CF_3$—$C_6H_4$ | H | —$C(CH_3)_2CCH$ |
| 55 | 3-$CF_3$—$C_6H_4$ | H | —$CH_2$-cyclo-$C_3H_5$ |
| 56 | 1-$CH_3$-3$CF_3$-pyrazol-5-yl | H | -4-F—$C_6H_4$ |
| 57 | 1-$CH_3$-3$CF_3$-pyrazol-5-yl | H | -3-F—$C_6H_4$ |
| 58 | 1-$CH_3$-3$CF_3$-pyrazol-5-yl | H | —$C_6H_5$ |
| 59 | 1-$CH_3$-3$CF_3$-pyrazol-5-yl | H | -cyclo-$C_3H_5$ |
| 60 | 1-$CH_3$-3$CF_3$-pyrazol-5-yl | H | -cyclo-$C_4H_7$ |
| 61 | 1-$CH_3$-3$CF_3$-pyrazol-5-yl | H | -n-$C_4H_9$ |
| 62 | 1-$CH_3$-3$CF_3$-pyrazol-5-yl | H | -2,4-F—$C_6H_3$ |
| 63 | 1-$CH_3$-3$CF_3$-pyrazol-5-yl | H | —$CH_2CF_3$ |
| 64 | 1-$CH_3$-3$CF_3$-pyrazol-5-yl | H | -cyclo-$C_6H_{11}$ |
| 65 | 1-$CH_3$-3$CF_3$-pyrazol-5-yl | H | -cyclo-$C_5H_9$ |
| 66 | 1-$CH_3$-3$CF_3$-pyrazol-5-yl | $CH_3$ | —$C_6H_5$ |
| 67 | 1-$CH_3$-3$CF_3$-pyrazol-5-yl | H | -1,2,4-triazole-1-yl |
| 68 | 1-$CH_3$-3$CF_3$-pyrazol-5-yl | H | -1,2,4-triazole-2-yl |
| 69 | 1-$CH_3$-3$CF_3$-pyrazol-5-yl | H | 3,5-F—$C_6H_3$ |
| 70 | 1-$CH_3$-3$CF_3$-pyrazol-5-yl | H | —$CH_2$-cyclo-$C_3H_5$ |
| 71 | 1-$CH_3$-3$CF_3$-pyrazol-5-yl | H | —$CH(CH_3)CH_2CH_3$ |
| 72 | 1-$CH_3$-3$CF_3$-pyrazol-5-yl | H | -3,4-F—$C_6H_3$ |
| 73 | 1-$CH_3$-3$CF_3$-pyrazol-5-yl | H | —O—$C(CH_3)_3$ |
| 74 | 1-$CH_3$-3$CF_3$-pyrazol-5-yl | H | morpholin-1-yl |
| 75 | 1-$CH_3$-3$CF_3$-pyrazol-5-yl | H | hexamethylenimin-1-yl |
| 76 | 1-$CH_3$-3$CF_3$-pyrazol-5-yl | —$CH_3$ | —$CH_3$ |
| 77 | 1-$CH_3$-3$CF_3$-pyrazol-5-yl | —$CH_2$—$CH_3$ | —$C_6H_5$ |
| 78 | 1-$CH_3$-3$CF_3$-pyrazol-5-yl | —$CH_2$—$CH_2$—$CH_3$ | —$CH_2$—$CH_2$—$CH_3$ |
| 79 | 1-$CH_3$-3$CF_3$-pyrazol-5-yl | —$CH_2$—$CH_2$—$CH_3$ | -3,4-F—$C_6H_3$ |

TABLE 6-continued

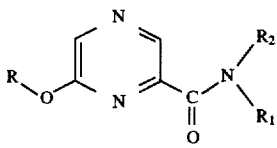

| Compound No. | R | $R_1$ | $R_2$ |
|---|---|---|---|
| 80 | 1-CH$_3$-3CF$_3$-pyrazol-5-yl | —CH$_2$CHCH$_2$ | —C$_6$H$_5$ |
| 81 | 1-CH$_3$-3CF$_3$-pyrazol-5-yl | —CH$_2$—C$_6$H$_5$ | —CH$_6$H$_5$ |
| 82 | 1-CH$_3$-3CF$_3$-pyrazol-5-yl | —CH$_2$—C$_6$H$_5$ | pyridyl-2-yl |
| 83 | 1-CH$_3$-3CF$_3$-pyrazol-5-yl | 2-CH$_3$-aziridin-1-yl | |
| 84 | 1-CH$_3$-3CF$_3$-pyrazol-5-yl | H | -2-F—C$_6$H$_4$ |
| 85 | 1-CH$_3$-3CF$_3$-pyrazol-5-yl | H | CH$_2$—CH$_2$—CH$_3$ |
| 86 | 3-CF$_3$-4-F-C$_6$H$_3$ | H | -4-F—C$_6$H$_4$ |
| 87 | 3-CF$_3$-4-F-C$_6$H$_3$ | H | —C$_6$H$_5$ |

Compound 88—6-(1-Methyl-3-trifluoromethylpyrazol-5-yloxy)-pyrazine-6-((N-methyl)(N-cyclopropyl) carboxamide 0.12g (4mmol) NaH were added at room temperature to a solution of 0.92g (2.8mmol) of compound 59 in 30 ml THF. After stirring for 15 min at 50° C. 1 ml of iodomethane was added and the resulting mixture as refluxed for 2 hours. After cooling 2 ml of water were added, the solvent was evaporated and the residue was solved in 10 ml of ethylacetate, washed with water and dried over Na$_2$SO$_4$. The solvent was evaporated and the residue was purified on silica gel using toluene/ethylacetate (2/1) as eluent to give 0.80 g (83.4%) of a brown oil.

NMR(CDCl$_3$): 0.3–0.5(m,4H,CH$_2$); 2.75(m,1H,CH); 3.13(s,3H, CH$_3$); 6.33(S, 1H, arom); 8.62(s. 1H, arom); 8.73(s, 1H arom);

Compounds of Table 7 have been prepared according to the procedure used for compound 88.

TABLE 7

| Compound No. | $R_1$ | $R_2$ | m.p. °C. | % yield |
|---|---|---|---|---|
| 89 | —CH$_3$ | 2-F—C$_6$H$_4$ | oil | 78.3 |
| 90 | —CH$_3$ | 3-F—C$_6$H$_4$ | 100–104 | 57.9 |
| 91 | —CH$_3$ | 4-F—C$_6$H$_4$ | 104–108 | 54.0 |
| 92 | —CH$_3$ | 2,4-F—C$_6$H$_3$ | oil | 67.2 |
| 93 | —CH$_3$ | 3,4-F—C$_6$H$_3$ | oil | 49.8 |
| 94 | —CH$_3$ | —CH$_2$—CF$_3$ | oil | 37.4 |
| 95 | —C$_2$H$_5$ | -n-C$_3$H$_7$ | oil | 43.3 |
| 96 | —C$_2$H$_5$ | cyclo-C$_3$H$_5$ | oil | 46.1 |
| 97 | —C$_2$H$_5$ | 4-F—C$_6$H$_4$ | oil | 39.2 |
| 98 | —C$_2$H$_5$ | 3,4-F—C$_6$H$_3$ | oil | 36.8 |
| 99 | —CH$_2$—CH$_2$—CH$_3$ | -3,4-F—C$_6$H$_3$ | oil | 75.1 |
| 100 | —CH$_2$CHCH$_2$ | cyclo-C$_3$H$_5$ | oil | 18.7 |
| 101 | —CH$_2$CHCH$_2$ | 4-F—C$_6$H$_4$ | oil | 47.1 |
| 102 | —CH$_2$CHCH$_2$ | 3,4-F—C$_6$H$_3$ | oil | 41.6 |

EXAMPLE 7

Preparation of 4-(3-trifluoromethyl)phenoxy-6-methylthio-1,3,5-triazine-2-(N-ethyl-N-phenyl) carboxamide Compound 30-3-Trifluoromethylphenylcyanate To an ice cold solution of 10 g 3-trifluoro-ethylphenol 250 ml acetone was added a solution of 6.54 g cyanogen bromide in 50 ml acetone and the resulting mixture was stirred for half an hour at 0° C. 6.25 g triethylamine were mixed with 20 ml acetone and added to the mixture and the resulting solution was stirred for another hour while warming to room temperature. The suspension was filtered and the mother liquor evaporated. The residue was dissolved in 50 ml of toluene and the precipitate was filtered off. The filtrate was evaporated to dryness to give 11.3 g (98.2%) of a pale yellow oil.

N-ethyl-N-phenyl-oxalic acid half anilide half chloride

To an ice cold solution of 4 g oxalylchloride in 60 toluene was added a solution of 3.81 g N-ethylaniline and 3.19 g triethylamine in 20 ml toluene over a period of 5 minutes and the resulting mixture was stirred for half an hour while maintaining the temperature at 0° C. The suspension was filtered, the residue was washed with 10 ml of ice cold toluene and the filtrate was evaporated to give 5 g (75.7%) of a brown oil, which was used for further reaction without any purification and isolation.

Compound 104—4-(3-trifluoromethyl)phenoxy-6-methylthio-1,3,5-triazine-2-(N-ethyl-N-phenyl) carboxamide To a solution of 5 g N-ethyl-N-phenyl-oxalyl half chloride half anilide (prepared as above) in 60 ml of dioxane was added a solution of 4.42 g 3-trifluoromethylphenyl cyanate over a period of 20 minutes and the resulting mixture was stirred for 2 hours at 50° C. After cooling to 10° C., 2.13 g isothiourea were added in one portion, followed by a solution of 4.78 g triethylamine in 50 ml dioxane. The mixture was stirred overnight at room temperature, filtered and the liquid evaporated to dryness.

The residue was dissolved in 250 ml ethyl acetate, washed twice with 50 ml dil. HCl, 50 ml water, twice with 50 ml dil. NaOH and again with 50 ml water. The organic layer was dried over Na$_2$SO$_4$ and evaporated. The residue was purified on silica gel with petroleum/ethyl acetate as eluent to give 0.18 g (1.75%, based on cyanate) of a yellow oil, identified as Compound 104.

EXAMPLE 8

Preparation of 2-(3-trifluoromethyl)phenoxy-6-methyl-pyrimidine-4-(N-(4-fluorophenyl)) carboxamide Compound 32—2-Chloro-4-cyano-6-methylpyrimidine 24.5 g of 2,4-dichloro-6-methylpyrimidine and 9.8 g of potassium cyanide were dissolved in 150 ml of $CH_3CN$ and refluxed for 8 days. The solvent was evaporated, the residue was dissolved in 150 ml of ethyl acetate and extracted twice with 50 ml $H_2O$. The organic layer was dried over $Na_2SO_4$, the solvent was evaporated and the residue was purified on silica gel using a 4:1 mixture of benzene and methyl tert.butyl ether as eluent to give 5.2 g (24.8%) of 2-chloro-4-cyano-6-methyl pyrimidine of m.p. 57° C.

Compound 106—2-(3-Trifluoromethyl)phenoxy-4-cyano-6-methyl-pyrimidine 5.1 g of compound 32 (prepared as above) and 6.73 g of 3-trifluoromethylphenol sodium salt were dissolved in 20 ml dimethylformamide and stirred for 4 hours at 110° C. The solvent was evaporated and the residue was dissolved in 50 ml $H_2O$ and the aqueous phase was extracted three times with 100 ml of of ethyl acetate. The combined organic layers were dried over $Na_2SO_4$, the solvent was evaporated and the residue was purified on silica gel with toluene/ethyl acetate as eluent to give 3.36 g (38.8%) of compound 33 with m.pt. 84°–86° C.

Compound 107—2-(3-Trifluoromethyl)phenoxy-6-methylpyrimidine-4-carboxylic acid 3.36 g of 2-(3-trifluoromethyl)phenoxy-4-cyano-6-methyl-pyrimidine were stirred in 20 ml of half conc. HCl for one hour at 80° C., diluted with 100 ml $H_2O$ and extracted twice with 100 ml of ethyl acetate. The organic layer was dried over $Na_2SO_4$, the solvent was evaporated and the residue was purified on silica gel using ethyl acetate followed by methanol as eluent to give 1.78 g (49.6%) of compound 34 (contaminated with silica gel) of m.p. >250° C.

Compound 108—2-(3-Trifluoromethyl)phenoxy-6-methylpyrimidine-4-(N-(4-fluorophenyl))carboxamide 1.77 g of compound 34 (prepared as above) were refluxed for 30 minutes in 5 ml of $SOCl_2$ and evaporated to dryness after cooling. The residue was dissolved in 50 ml toluene, evaporated and dissolved again in 50 ml toluene. This solution was added dropwise to a solution of 0.66 g 4-fluoroaniline and 0.6 g triethylamine in 5 ml toluene and stirred for 1 hour room temperature. The solution was extracted twice with 25 ml water. The water layer was extracted with 25 ml of dil. HCl, followed by 25 ml of dil. NaOH and then with 50 ml water. The organic layers were combined and dried over $Na_2SO$. The solvent was evaporated and the residue was purified on silica gel with toluene/ethyl acetate to give 0.4 g (17.2%) of compound 35 as a brown oil.

NMR ($CDCl_3$): 2.65(s,3H,$CH_3$); 6.9(s,1H,Arom.); 7.0(m, 2H,Arom.);
7.4(m,1H,Arom.); 7.5(m,1H,Arom.), 7.6(m,4H,Arom.); 9.5(s,1H,NH).

Compound 109—2-Thiomethyl-4-(2-chloropyrid-4-yloxy)-6-(N,N-dimethylamino)pyrimindine According to the procedure for compound 16, compound 109 has been prepared in 45.2% with m.p. 98°–99° C.

Compound 110—2-Methylsulfonyl-yl-4-(2-chloropyrid-4-yloxy)-6-(N,N-dimethylamino)pyrimidine Following the procedure for compound 17, compound 110 has been prepared in 54.7% yield with m.p. 89° C.

Compound 111—2-Cyano-4-(2-chloropyrid-4-yloxy)-6-(N,N-dimethylamino)pyrimidine

According to the procedure described for compound 18, compound 111 has been prepared in 40.8% with m.p. 98°–108° C.

Compound 112—4-(2-chloropyrid-4-yloxy)-6-(N,N-dimethylamino)-pyrimidine-2-(N-(4-fluorophenyl) carboxamide Compound 112 has been prepared following the procedure for compound 20 in 91.1% with m.p. 157°–163° C.

TABLE 8

Elemental Analysis

| Compound No. | Calc. | | | Found | | |
|---|---|---|---|---|---|---|
| | C (%) | (H (%) | N (%) | C (%) | H (%) | N (%) |
| 1 | 54.35 | 2.28 | 15.85 | 52.67 | 3.49 | 13.65 |
| 2 | 50.89 | 2.85 | 14.84 | 51.18 | 3.19 | 14.43 |
| 3 | 50.72 | 2.48 | 9.86 | 48.96 | 2.96 | 13.91 |
| 4 | 55.25 | 2.83 | 14.32 | 57.25 | 3.13 | 11.10 |
| 5 | 60.17 | 3.37 | 11.69 | 59.08 | 3.75 | 11.13 |
| 6 | 62.01 | 4.16 | 10.85 | 62.59 | 4.57 | 10.37 |
| 7 | 56.64 | 4.75 | 12.38 | 56.78 | 4.69 | 12.26 |
| 8 | 54.69 | 2.55 | 10.63 | 55.11 | 3.17 | 10.46 |
| 9 | 55.79 | 3.74 | 13.00 | 55.93 | 3.96 | 12.63 |
| 10 | 55.24 | 2.53 | 11.71 | 54.97 | 2.76 | 11.09 |
| 11 | 54.35 | 2.28 | 15.85 | 54.11 | 2.26 | 15.55 |
| 12 | 50.89 | 2.85 | 14.84 | 51.06 | 3.04 | 15.76 |
| 13 | 50.72 | 2.48 | 9.86 | 49.98 | 3.13 | 9.75 |
| 14 | 57.30 | 2.94 | 11.14 | 57.24 | 2.98 | 11.25 |
| 15 | 41.28 | 4.95 | 20.63 | 41.30 | 4.87 | 20.25 |
| 16 | 51.05 | 4.28 | 12.75 | 50.58 | 4.28 | 13.42 |
| 17 | 46.54 | 3.90 | 11.63 | 47.41 | 4.20 | 10.74 |
| 18 | 54.55 | 3.60 | 18.18 | 54.83 | 3.99 | 18.74 |
| 19 | 51.38 | 3.70 | 12.84 | 51.09 | 3.73 | 12.93 |
| 20 | 57.15 | 3.84 | 13.33 | 57.15 | 4.31 | 13.23 |
| 21 | 54.80 | 3.45 | 12.78 | 54.90 | 4.17 | 12.73 |
| 22 | 59.70 | 4.26 | 13.92 | 58.32 | 4.89 | 13.47 |
| 23 | 61.39 | 4.92 | 13.92 | 61.67 | 5.32 | 12.51 |
| 25 | 55.26 | 5.30 | 18.41 | 54.21 | 5.34 | 17.60 |
| 26 | 50.00 | 4.79 | 16.66 | 49.63 | 4.73 | 15.97 |
| 28 | 53.85 | 3.55 | 8.97 | 53.69 | 3.48 | 8.82 |
| 31 | 50.72 | 2.48 | 9.86 | 50.95 | 2.86 | 10.20 |
| 34 | 55.25 | 2.83 | 14.32 | 57.95 | 2.86 | 10.20 |
| 103 | 51.35 | 2.15 | 7.49 | 51.53 | 2.89 | 7.13 |
| 104 | 57.63 | 3.74 | 12.22 | 58.23 | 3.66 | 11.98 |
| 105 | 51.61 | 2.87 | 20.07 | 50.89 | 2.56 | 20.56 |
| 106 | 65.82 | 3.37 | 17.72 | 65.39 | 3.21 | 17.98 |
| 107 | 60.94 | 3.51 | 10.94 | 60.65 | 3.73 | 10.04 |
| 108 | 58.31 | 3.32 | 10.74 | 58.12 | 3.19 | 11.01 |
| 24 | 51.49 | 3.98 | 17.16 | 51.03 | 4.29 | 17.39 |
| 35 | 54.64 | 2.53 | 10.63 | 54.98 | 2.92 | 11.16 |
| 36 | 61.96 | 4.13 | 10.84 | 61.84 | 4.37 | 10.92 |
| 37 | 57.25 | 2.92 | 11.13 | 57.56 | 3.30 | 11.41 |
| 38 | 54.39 | 3.99 | 11.89 | 54.23 | 4.06 | 11.78 |
| 16a | 48.57 | 4.41 | 18.88 | 48.37 | 4.12 | 18.66 |
| 17a | 43.84 | 3.98 | 17.04 | 43.64 | 3.65 | 16.59 |
| 18a | 52.28 | 3.66 | 25.40 | 52.46 | 3.96 | 25.42 |
| 20a | 55.75 | 3.90 | 18.06 | 55.82 | 4.00 | 17.14 |

EXAMPLE 9

Herbicidal Activity

To evaluate their herbicidal activity, compounds according to the invention were tested using as representative range of plants: maize, Zea mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 5 below, in which the compounds are identified by reference to the preceding Compound Nos. allocated in Examples 1 to 8 above. Absence of a numeral indicates that no test was carried out; an asterisk indicates that no result was obtained.

TABLE 5

| Compound No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 2 | 3 | 0 | 4 | 3 | 0 | 4 | 2 | 0 | 5 | 0 | 0 | 4 | 0 | 2 | 4 | 2 | 5 | 0 | 0 | 0 | 0 | 0 | 3 | 0 | 0 |
| | | | | | | | | | 1 | 0 | 0 | 0 | 0 | 0 | 0 | 0 | 4 | 0 | 0 | 0 | 0 | 0 | 0 | 0 | 0 |
| 3 | 0 | 0 | 0 | 0 | 0 | 0 | 0 | 0 | 5 | 0 | 0 | 2 | 0 | 3 | 4 | 3 | 5 | 0 | 0 | 0 | 0 | 0 | 0 | 0 | 0 |
| | | | | | | | | | 1 | 0 | 0 | 0 | 0 | 0 | 2 | 0 | 2 | 0 | 0 | 0 | 0 | 0 | 0 | 0 | 0 |
| 4 | 4 | 0 | 5 | 4 | 3 | 4 | 2 | 0 | 5 | 5 | 0 | 8 | 5 | 6 | 8 | 9 | 6 | 2 | 0 | 5 | 2 | 4 | 9 | 8 | 4 |
| | | | | | | | | | 1 | 4 | 0 | 7 | 2 | 6 | 7 | 9 | 4 | 0 | 0 | 2 | 0 | 0 | 8 | 7 | 0 |
| 5 | 0 | 0 | 0 | 0 | 0 | 3 | 0 | 0 | 5 | 5 | 0 | 7 | 3 | 5 | 9 | 9 | 6 | 1 | 0 | 3 | 0 | 0 | 8 | 8 | 0 |
| | | | | | | | | | 1 | 2 | 0 | 4 | 0 | 4 | 8 | 8 | 5 | 0 | 0 | 1 | 0 | 0 | 7 | 6 | 0 |
| 6 | 0 | 0 | 0 | 0 | 0 | 3 | 0 | 0 | 5 | 4 | 0 | 3 | 2 | 4 | 9 | 9 | 5 | 0 | 0 | 0 | 0 | 0 | 6 | 6 | 2 |
| | | | | | | | | | 1 | 2 | 0 | 2 | 0 | 3 | 8 | 8 | 4 | 0 | 0 | 0 | 0 | 0 | 5 | 2 | 0 |
| 7 | 0 | 0 | 0 | 0 | 0 | 0 | 0 | 0 | 5 | 4 | 0 | 3 | 2 | 3 | 7 | 6 | 4 | 0 | 0 | 0 | 0 | 0 | 2 | 2 | 0 |
| | | | | | | | | | 1 | 2 | 0 | 0 | 0 | 0 | 6 | 4 | 2 | 0 | 0 | 0 | 0 | 0 | 1 | 1 | 0 |
| 8 | 0 | 0 | 0 | 0 | 0 | 0 | 0 | 0 | 5 | 4 | 0 | 4 | 3 | 6 | 8 | 9 | 7 | 0 | 0 | 4 | 0 | 0 | 7 | 7 | 2 |
| | | | | | | | | | 1 | 2 | 0 | 3 | 2 | 2 | 8 | 7 | 5 | 0 | 0 | 2 | 0 | 0 | 7 | 6 | 0 |
| 9 | 0 | 0 | 0 | 0 | 0 | 5 | 3 | 2 | 5 | 4 | 0 | 6 | 4 | 4 | 8 | 8 | 4 | 3 | 0 | 4 | 2 | 0 | 4 | 8 | 2 |
| | | | | | | | | | 1 | 2 | 0 | 2 | 0 | 2 | 6 | 6 | 2 | 0 | 0 | 2 | 0 | 0 | 2 | 3 | 0 |
| 11 | 0 | 0 | 0 | 0 | 0 | 0 | 0 | 0 | 5 | 5 | 0 | 2 | 0 | 2 | 4 | 4 | 3 | 0 | 0 | 0 | 0 | 0 | 0 | 0 | 0 |
| | | | | | | | | | 1 | 0 | 0 | 0 | 0 | 0 | 2 | 0 | 0 | 0 | 0 | 0 | 0 | 0 | 0 | 0 | 0 |
| 14 | 0 | 0 | 0 | 0 | 0 | 0 | 0 | 0 | 5 | 6 | 0 | 8 | 4 | 6 | 9 | 9 | 5 | 2 | 0 | 3 | 2 | 3 | 8 | 4 | 0 |
| | | | | | | | | | 1 | 4 | 0 | 4 | 2 | 5 | 8 | 9 | 4 | 0 | 0 | 2 | 0 | 0 | 8 | 2 | 0 |
| 18 | | * | * | * | * | * | * | | 5 | | 4 | 2 | 0 | 4 | 7 | 6 | | 0 | 2 | 1 | 0 | 4 | 5 | | |
| | | | | | | | | | 1 | | 2 | 0 | 0 | 2 | 5 | 3 | | 0 | 0 | 0 | 0 | 3 | 2 | | |
| 19 | 0 | 0 | 0 | 0 | 0 | 0 | 0 | 0 | 5 | 0 | 0 | 2 | 0 | 0 | 8 | 0 | 0 | 0 | 0 | 0 | 0 | 0 | 2 | 0 | 0 |
| | | | | | | | | | 1 | 0 | 0 | 0 | 0 | 0 | 7 | 0 | 0 | 0 | 0 | 0 | 0 | 0 | 0 | 0 | 0 |
| 20 | 0 | 0 | 1 | 4 | 2 | 5 | 2 | 0 | 5 | 5 | 0 | 6 | 2 | 4 | 9 | 8 | 4 | 0 | 0 | 0 | 0 | 0 | 8 | 7 | 0 |
| | | | | | | | | | 1 | 2 | 0 | 2 | 0 | 2 | 8 | 7 | 2 | 0 | 0 | 0 | 0 | 0 | 8 | 6 | 0 |
| 21 | 0 | 0 | 0 | 4 | 0 | 4 | 2 | 0 | 5 | 0 | 0 | 0 | 0 | 0 | 7 | 6 | 0 | 0 | 0 | 0 | 0 | 0 | 6 | 4 | 0 |
| | | | | | | | | | 1 | 0 | 0 | 0 | 0 | 0 | 7 | 5 | 0 | 0 | 0 | 0 | 0 | 0 | 6 | 2 | 0 |
| 22 | 3 | 0 | 5 | 6 | 4 | 5 | 6 | 0 | 5 | 5 | 0 | 7 | 4 | 6 | 7 | 8 | 4 | 0 | 0 | 0 | 0 | 2 | 8 | 7 | 2 |
| | | | | | | | | | 1 | 2 | 0 | 2 | 0 | 4 | 7 | 8 | 3 | 0 | 0 | 0 | 0 | 0 | 7 | 7 | 0 |
| 23 | 4 | 0 | 5 | 1 | 2 | 4 | 2 | 0 | 5 | 5 | 0 | 6 | 1 | 2 | 6 | 8 | 4 | 0 | 0 | 1 | 0 | 0 | 7 | 8 | 2 |
| | | | | | | | | | 1 | 1 | 0 | 2 | 0 | 0 | 5 | 8 | 2 | 0 | 0 | 0 | 0 | 0 | 7 | 8 | 0 |
| 28 | 0 | 0 | 0 | 0 | 0 | 0 | 0 | 0 | 5 | 0 | 0 | 2 | 0 | 6 | 5 | 6 | 4 | 0 | 0 | 0 | 0 | 0 | 0 | 0 | 0 |
| | | | | | | | | | 1 | 0 | 0 | 0 | 0 | 5 | 2 | 2 | 3 | 0 | 0 | 0 | 0 | 0 | 0 | 0 | 0 |
| 29 | 4 | 0 | 6 | 2 | 3 | 6 | 2 | 0 | 5 | 6 | 6 | 8 | 7 | 6 | 8 | 9 | 8 | 2 | 0 | 7 | 2 | 2 | 5 | 6 | 0 |
| | | | | | | | | | 1 | 5 | 4 | 7 | 6 | 5 | 8 | 9 | 7 | 0 | 0 | 6 | 0 | 0 | 4 | 4 | 0 |
| 35 | 0 | 0 | 0 | 0 | 0 | 6 | 7 | 0 | 5 | 5 | 4 | 8 | 6 | 6 | 8 | 9 | 6 | 2 | 0 | 4 | 3 | 4 | 8 | 9 | 4 |
| | | | | | | | | | 1 | 2 | 0 | 2 | 5 | 5 | 7 | 9 | 2 | 1 | 0 | 0 | 2 | 3 | 7 | 9 | 2 |
| 36 | 4 | 0 | 5 | 0 | 2 | 6 | 5 | 4 | 5 | 0 | 0 | 6 | 2 | 6 | 8 | 8 | 7 | 0 | 0 | 7 | 0 | 5 | 8 | 8 | 5 |
| | | | | | | | | | 1 | 0 | 0 | 2 | 0 | 5 | 8 | 7 | 6 | 0 | 0 | 2 | 0 | 2 | 6 | 5 | 4 |
| 37 | 4 | 0 | 6 | 3 | 4 | 5 | 3 | 0 | 5 | 6 | 3 | 8 | 5 | 6 | 9 | 9 | 6 | 5 | 1 | 6 | 4 | 1 | 8 | 9 | 0 |
| | | | | | | | | | 1 | 5 | 0 | 7 | 4 | 6 | 8 | 9 | 4 | 4 | 0 | 5 | 4 | 0 | 8 | 8 | 0 |
| 38 | 4 | 0 | 3 | 4 | 5 | 7 | 8 | 0 | 5 | 4 | 0 | 8 | 6 | 7 | 8 | 9 | 7 | 0 | 0 | 7 | 0 | 2 | 8 | 8 | 0 |
| | | | | | | | | | 1 | 2 | 0 | 5 | 4 | 6 | 8 | 8 | 6 | 0 | 0 | 2 | 0 | 0 | 8 | 8 | 0 |
| 39 | 0 | 0 | 0 | 0 | 4 | 4 | 3 | 1 | 5 | 6 | 2 | 7 | 2 | 5 | 9 | 9 | 5 | 2 | 0 | 6 | 2 | 2 | 8 | 7 | 2 |
| | | | | | | | | | 1 | 4 | 0 | 5 | 0 | 5 | 8 | 8 | 5 | 0 | 0 | 5 | 0 | 2 | 7 | 6 | 0 |
| 16(A) | 4 | 0 | 5 | 0 | 6 | 1 | 6 | 0 | 5 | 0 | 0 | 4 | 0 | 5 | 8 | 9 | 6 | 0 | 0 | 0 | 0 | 0 | 0 | 0 | 0 |
| | | | | | | | | | 1 | 0 | 0 | 2 | 0 | 4 | 8 | 8 | 2 | 0 | 0 | 0 | 0 | 0 | 0 | 0 | 0 |
| 18(A) | 6 | 5 | 6 | 4 | 3 | 5 | 2 | 0 | 5 | 0 | 0 | 7 | 0 | 4 | 8 | 8 | 7 | 3 | 2 | 6 | 4 | 3 | 6 | 4 | 0 |
| | | | | | | | | | 1 | 0 | 0 | 2 | 0 | 2 | 8 | 7 | 5 | 0 | 0 | 5 | 0 | 1 | 5 | 2 | 0 |

We claim:
1. A compound of the formula (I)

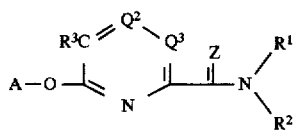

wherein

A represents a group of formula

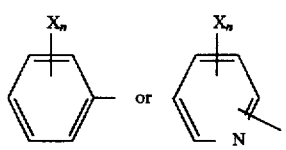

in which the or each X independently represents a halogen atom or an optionally substituted alkyl, alkoxy, phenyl or phenyloxy group or an alkenyloxy, alkynyloxy, alkylthio, haloalkylthio, alkenylthio, alkynylthio, alkylsulphinyl, alkylsulphonyl or cyano group, and n is 0 or an integer from 1 to 4, or, for the phenyl group, 5; or A represents a group of the formula

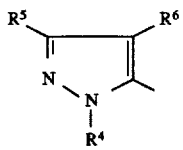

in which $R^4$ represents a hydrogen or halogen atom or an optionally substituted alkyl, alkenyl, alkynyl, cycloalkyl, cycloalkylalkyl, phenyl, phenylalkyl, alkylphenyl, alkoxy, amino, mono- or dialkylamino, alkoxycarbonylamino, phenylamino, dialkylcarbamoyl, acyl or acylamido group or a cyano group;

each of $R^5$ and $R^6$ independently represents a hydrogen or halogen atom or an optionally substituted alkyl, alkenyl, alkynyl, cycloalkyl, cycloalkylalkyl, phenyl, phenylalkyl, alkylphenyl, alkoxy, amino, mono- or dialkylamino, alkoxycarbonylamino, phenylamino, dialkylcarbamoyl group;

Z represents an oxygen or atom;

$R^1$ and $R^2$ each independently represent a hydrogen atom or an optionally substituted alkyl, alkenyl, alkynyl, cycloalkyl, cycloalkylalkyl, phenyl, phenylalkyl, alkylphenyl, hydroxyl, alkoxy, alkenyloxy, alkynyloxy, alkylcarbonyl, alkoxycarbonyl, amino, mono- or dialkylamino, alkoxycarbonylamino, phenylamino, phenylalkylamino or dialkylcarbamoyl group; or $R^1$ and $R^2$ together represent an alkylene chain having 3 to 6 chain members;

$R^3$ represents a hydrogen atom or an optionally substituted alkyl, alkoxy, alkenyloxy, alkylthio or mono- or dialkylamino group; and $Q^2$ represents a nitrogen atom and $Q^3$ represents $CR^3$;

in which any alkyl, alkenyl or alkynyl moiety which is or forms part of a group $R^1$, $R^2$, $R^3$, $R^4$, $R^5$, $R^6$ or X contains up to 12 carbon atoms, any cycloalkyl moiety which is or forms part of a group $R^1$, $R^2$, $R^4$, $R^5$ or $R^6$ contains 3 to 10 carbon atoms, any heterocyclyl moiety which is or forms part of a group $R^1$ or $R^2$ is a single ring system having 3 to 6 ring members selected from carbon atoms and at least one nitrogen, oxygen or sulfur atom;

and in which optional substituents of the groups $R^1$, $R^2$, $R^4$, $R^5$, $R^6$ or X are selected from the group consisting of halogen atoms, and phenyl, nitro, cyano, amino, hydroxyl, alkyl, alkoxy, mono- or dialkylamino groups, and haloalkyl, haloalkoxy, formyl alkoxycarbonyl carboxy, halophenyl groups and thienyl groups, in which any alkyl moiety of such optional substituents have 1 to 6 carbon atoms.

2. A compound as claimed in claim 1, wherein A represents a group

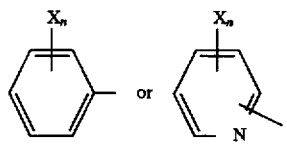

in which X represents a halogen atom or a halo($C_{1-2}$)alkyl group and n is 0 or 1, or A represents a group

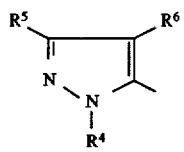

in which $R^4$ and $R^5$ independently represents a $C_{1-4}$ alkyl group or a halo($C_{1-2}$)alkyl group.

3. A compound as claimed in claim 1, wherein $R^1$ and $R^2$ each independently represents a hydrogen atom, a $C_{1-6}$ alkyl group, a C3-6 cycloalkyl group or an unsubstituted or halo-substituted phenyl group.

4. A compound as claimed in claim 1, wherein $R^3$ represents a hydrogen atom, a $C_{1-4}$ alkyl group or a di($C_{1-4}$)-alkylamino group.

5. A compound as claimed in claim 1, wherein A represents a 3-trifluoromethylphenyl group, one of $R^1$ and $R^2$ represents a hydrogen atom or a $C_{1-4}$ alkyl group and the other represents a halophenyl group.

6. A compound as claimed in claim 1 selected from the group consisting of 6-(3-trifluoromethylphenoxy)-pyrazine-2-(N-(4-fluorophenyl))carboxamide;

6-(3-trifluoromethylphenoxy)-pyrazine-2-(N-(2,4-difluorophenyl))carboxamide;

6-(3-trifluoromethylphenoxy)-pyrazine-2-(N-ethyl-N-phenyl)carboxamide;

6-(3-trifluoromethylphenoxy)-pyrazine-2-(N-(2-fluorophenyl))carboxamide; and 6-(1-methyl-3-trifluoromethylpyrazol-5-oxy)-pyrazine-2-(N-4fluorophenyl))carboxamide.

7. A herbicidal composition comprising at least one compound of general formula I, as claimed in claim 1, together with a carrier.

8. A method of combating undesired plant growth at a locus, comprising application to the locus with a compound of formula I, as claimed in claim 1.

* * * * *